United States Patent [19]

Collazo

[11] Plant 5,182

[45] Jan. 24, 1984

[54] MINIATURE ROSE PLANT-WHITE CHIPPER VARIETY

[75] Inventor: Ezequiel Collazo, West Grove, Pa.

[73] Assignee: The Conard-Pyle Company, West Grove, Pa.

[21] Appl. No.: 393,864

[22] Filed: Jun. 30, 1982

[51] Int. Cl.[3] ..... A01H 5/00

[52] U.S. Cl. ..... Plt./8

[58] Field of Search ..... Plt./8

*Primary Examiner*—Robert E. Bagwill

*Attorney, Agent, or Firm*—Burns, Doane, Swecker & Mathis

[57] ABSTRACT

A new and distinct variety of Miniature rose plant is provided having highly attractive double blossoms which are white with an occasional pink tint. The new variety is a mutation of the Chipper variety (U.S. Plant Pat. No. 2,764) which is known to bear coral pink blossoms. Other than the blossom coloration the characteristics of the new variety generally correspond to those of the Chipper variety.

1 Drawing Figure

SUMMARY OF THE INVENTION

The object of the present invention is to provide a new variety of rose plant of the Miniature class which is distinguished from prior varieties by the following combination of characteristics:

(a) from the physical standpoint the plant is substantially identical to that of the parent Chipper variety with the exception of blossom coloration, has an almost erect growth habit, forms light green shiny leaves, and forms very double flowers which are white with an occasional pink blush during the cooler months; and (b) from the biological standpoint the plant has vigorous and regular vegetation, exhibits an abundant and repeated florescence, and possesses the ability of its blossoms to last for extended periods whether on the bush or cut.

The new variety resulted as a spontaneous sport of unknown causation of the Miniature rose variety Chipper, which I discovered among plants of such variety growing at The Conard-Pyle Co., West Grove, Pa. Such discovery was made while I was performing my duties as rose propagator for that company.

The characteristics and properties of this new variety have been found to be transmissible by vegetative propagation through cuttings, grafting and budding performed at West Grove, Pa.

The rose plant of the new variety has been named, the White Chipper variety.

BRIEF DESCRIPTION OF THE PHOTOGRAPH

The accompanying photograph shows as nearly true as it is possible to make the same in a color illustration of this character, typical specimens of plant parts from two year old plants produced from softwood cuttings and growing in the open air during mid-June at West Grove, Pa.

In the upper left portion of the photograph is shown a specimen of four buds following the opening of the sepals.

In the upper left center portion of the photograph is shown a specimen of foliage and a single bud before the opening of the sepals.

In the upper right portion of the photograph four blossoms are shown in various stages of opening.

In the right center portion of the photograph are shown a leaf with five leaflets and a leaf with seven leaflets.

In the lower portion of the photograph is shown a segment of a main branch from which extends a flowering stem.

DETAILED DESCRIPTION

The plants described were grown outdoors during June at West Grove, Pa.

The chart utilized in the identification of the colors is that of The Royal Horticultural Society (R.H.S. Colour Chart).

Class: Miniature.

Plant:

*Height.*—30 to 40 cm. on average.

*Bearing.*—Erect.

Branches:

*Color.*—Young stems: Light green, Yellow-Green Group 144B, with faint red shading. Mature wood: Light green, Yellow-Green Group 144A.

*Thorns.*—Shape of upper edge: Straight to slightly convex. Shape of lower edge: Concave. Size: Medium. Color: Red, fading slightly on older wood.

Foliage:

*Stipules.*—Adnate, doubly serrate, narrow and linear with red tint to edges.

*Petiole.*—Inner surface: Grooved, reddish green (young leaves), and light green (mature wood), tomentulose, with prickles along edges. Outer surface: Pale red-green (young wood), and pale green (mature wood) with mostly glandular surface.

*Leaflets.*—Number: 3 occasionally, but 5 or 7 more often. Shape: Elliptical, rounded base, length approximately 2 cm.; average width approximately 1 cm. Teeth: Serrulate. General effect: Leaves broadly spaced, airy.

*Color.*—Young leaves: Upper surface: Medium green, Green Group 143B, with Greyed-Red Group 180B tones. Under surface: Light green, Yellow-Green Group 144C. Mature leaves:

Upper surface: Light green, lighter than Green Group 143C. Under surface: Light green, Yellow-Green Group 145B.

Flowers:

*Number of flowers.*—Commonly three to five flowers per stem, but will vary between one and six flowers per stem.

*Peduncle.*—Slight curve in direction of main stem, tomentose, bears some red prickles, approximately 2.5 to 3.5 cm. in length.

*Sepals.*—Inner surface: Light green with white cast, tomentose, often incised. Outer surface: Light green, usually with bronze tint, tomentulose, often foliaceous.

*Bud.*—Ovate with thick neck. Length: Approximately 1 to 1.5 cm. at opening of sepals. Size: Medium. Color on opening: White with pink blush, Red Group 49C. The degree of pink coloration depends upon the weather conditions with the pink being more pronounced during the cooler months.

*Flower.*—Shape: Flat, with outer petals recurving toward the peduncle. Diameter: 3 to 4 cm. on average. Color: When first opening the center can be pink, Red Group 49B, or lighter depending upon weather conditions, and during hot bright periods will be almost pure white. The outer petals are usually white. When fully open the pink usually fades to almost pure white. Fragrance: None. Lasting quality: Long, both on bush and cut. Texture: Firm. Petal shape: Obovate, with pale yellow claw. Number of petals: Approximately 65 to 75 petals. Pistils: Approximately 45 on average with pale green stigmas and reddish styles. Stamens: 18 on average, and ochre in color. Receptacle: Pale green with obtuse shape.

Development:

*Vegetation.*—Vigorous and regular.

*Flowering.*—Abundant and repeated throughout the growing season.

*Capacity for bearing fruit.*—Average.

*Resistance to frost.*—Average for class.

*Resistance to diseases.*—Average for class.

I claim:

1. A new and distinct variety of Miniature rose plant, substantially as illustrated and described, wherein:

(a) from the physical standpoint the plant is substantially identical to that of the parent Chipper variety with the exception of the blossom coloration, has an almost erect growth habit, forms light green shiny leaves, and forms very double flowers which are white with an occasional pink blush during the cooler months; and (b) from the biological standpoint the plant has vigorous and regular vegetation, exhibits an abundant and repeated florescence, and possesses the ability of its blossoms to last for extended periods whether on the bush or cut.

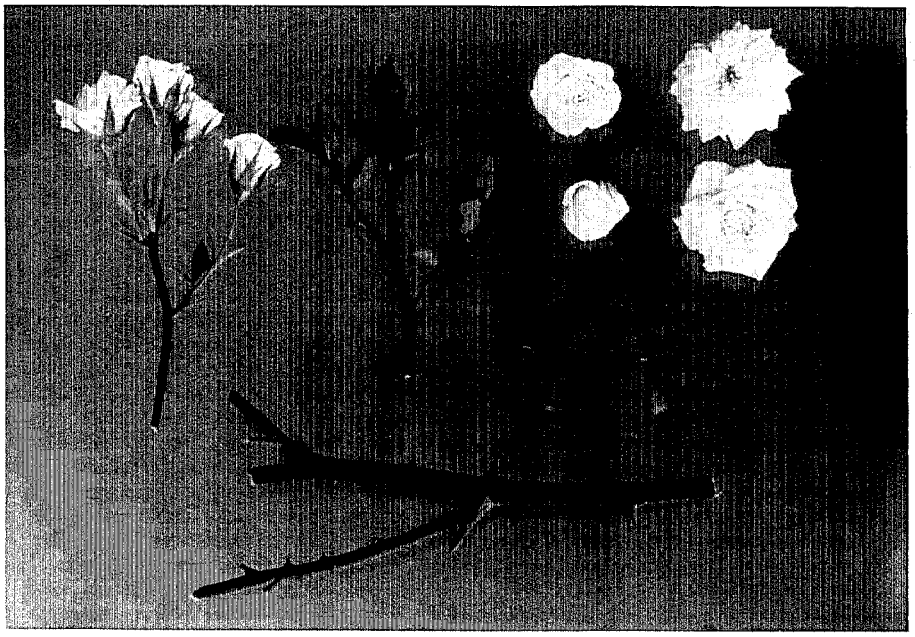

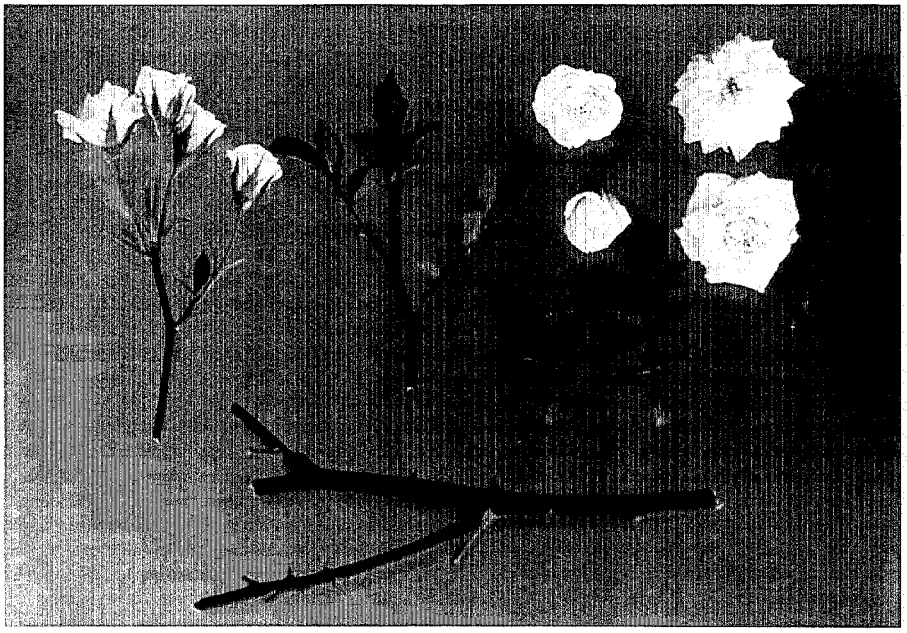

* * * * *